United States Patent [19]

Bell

[11] Patent Number: 5,128,466
[45] Date of Patent: Jul. 7, 1992

[54] CYCLIC COMPOUNDS FOR COMPLEXING WITH CATIONS

[75] Inventor: Thomas W. Bell, Miller Place, N.Y.

[73] Assignee: The Research foundation of State University of New York, Albany, N.Y.

[21] Appl. No.: 423,038

[22] Filed: Oct. 18, 1989

[51] Int. Cl.$^5$ ............................................ C07D 257/02
[52] U.S. Cl. .................................... 540/452; 540/453; 204/418
[58] Field of Search .......................... 540/453; 340/452

[56] References Cited

U.S. PATENT DOCUMENTS 4,987,227  1/1991  Burrows et al. .................... 540/452

OTHER PUBLICATIONS

Metzger, E., et al., Anal. Chem. 59, 1600–1603 (1987).
Moody, G. J., et al., Chemical Sensors, (T. E. Edmonds, Ed.), Blackie, Chapman & Hall, New York, 1988, Chap. 3, pp. 102–116.
Kimura, K., et al., Anal. Chem. 59, 2331–2334 (1987).
Xie, R. Y., et al., Analyst 112, 61–64 (1987).
Erne, D., et al., Helv. Chim. Acta 65, 538–545 (1982).
Metzger, E., et al., Chimia 38, 440–442 (1984).
Metzger, E., et al., Anal. Chem. 58, 132–135 (1986).
Metzger, E., et al., Helv. Chim. Acta 69, 1821–1828 (1986).
Gadzekpo, V. P. Y., et al., Anal. Chem. 58, 1948–1953 (1986).
Adamcik, J. A., et al., J. Org. Chem. 28, 336–339 (1963).
Sury, E., et al., Helv. Chim. Acta 36, 1815–1821 (1953).
Fones, W. S., J. Org. Chem. 14, 1099–1102 (1949).
Hatt, H. H., Chem. Abs. 72: 132667u (1970).
Attiyat, A. S., et al., Chem. Abs. 108: 160433v (1988).

Primary Examiner—Robert T. Bond
Attorney, Agent, or Firm—Hoffmann & Baron

[57] ABSTRACT

Cyclic molecules having oriented groups are capable of forming stable complexes with cations.

20 Claims, No Drawings

CYCLIC COMPOUNDS FOR COMPLEXING WITH CATIONS

BACKGROUND OF THE INVENTION

This invention relates to novel compositions of matter which are ion-complexing agents, to the use of the agents to detect cations, and to complexes of the compounds with cations.

Lithium is present in the blood of patients undergoing therapy for manic depression. It is important to maintain effective serum lithium levels for optimum treatment and at the same time the likelihood of lithium toxicity increases with increased serum lithium levels. Therefore, it is important to carefully monitor blood lithium levels in these patients.

Clinical chemistry analyzers can utilize ion-selective electrodes (ISE's) for direct potentiometric determination of levels of cations such as those of sodium and potassium in blood serum, plasma and urine. Clinical analysis of lithium in these human bodily fluids, however, requires an ISE with high selectivity for lithium relative to sodium and potassium which are likely to be present with lithium. Suitable ionophores have not been available with the required selectivity of less than 1% interference by sodium (Metzger, et al., *Anal. Chem.* 1987, 59, 1600–1603). In addition, a microelectrode selective for lithium would also have important applications in biomedical research for detecting local ion concentrations in tissues such as nerve fibers.

Lithium ISE's based on crown compounds and acyclic compounds are known (Moody et al., *Chemical Sensors*, Edmonds, Ed., Chapman & Hall, New York (1988) Chpt. 3). Derivatives of 14-crown-4 ethers selective for Li+ have been described (Kimura et al., *Anal. Chem.* 1987 59, 2331–2334; Xie et al., *Analyst* 1987 112, 61–64). Lithium selectivity in acyclic diamides with bidentate ligands has also been described (Metzger et al., *Chimia* 1984 38, 440–442; Metzger et al., *Anal. Chem.* 1986 58, 132–135; Metzger et al., *Anal. Chem.* 1987 59, 1600–1603); and lithium selectivity in acyclic diamides with quadridentate ligands has been described (Metzger et al., *Helvetica Chimica Acta* 1986 69, 1821–1828; Metzger et al., *Anal. Chem.* 1987 59, 1600–1603). Lithium-selective ionophores which are bi-, tri- and quadridentate have also been described (Gadzekpo et al., *Anal. Chem.* 1986 58, 1948–1953).

In addition, the synthesis of spirodiimides has been disclosed (Adamcik et al., *J. Org. Chem.*, 1963, Vol. 28, 336–339) and the alkylation of 2,5-dioxopyrrolidine has been described (Sury et al., *Helv. Chim. Acta* 1953 26, 1815–1821). However, these articles disclose only basic synthetic methods and do not suggest the complexing agents of the invention.

A new approach in providing complexing agents with adjustable ion selectivity is highly desirable. An object of the invention is to provide such complexing agents. It is a specific object to provide a new family of compounds which selectively complex with lithium ions relative to sodium and potassium ions and which can be modified to vary selectivity for complexation with other cations. It is yet another object to provide stable complexes of these compounds with ions.

SUMMARY OF THE INVENTION

The invention concerns molecules having the Structure I.

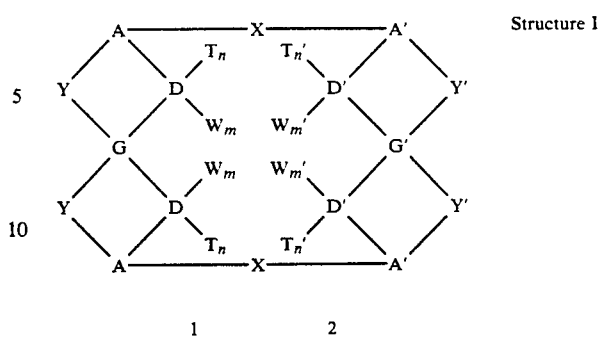

Structure I wherein

A and A' independently represent carbon or nitrogen atoms;

D and D' independently represent carbon, nitrogen, oxygen, sulfur or phosphorus atoms;

G and G' independently represent carbon or silicon atoms;

T and T' independently represent an oxygen atom or a radical R;

W and W' independently represent an oxygen atom or a radical R;

R represents an alkyl or aryl group with from 1 to 12 carbon atoms, or OR' wherein O independently represents an oxygen atom and R' represents an alkyl or aryl group with from 1 to 12 carbon atoms;

m represents 0 or 1;

n represents 0 or 1;

Y and Y' independently represent a hydrocarbon or heterocarbon group having from 1 to 10 members; and X independently represents a hydrocarbon or heterocarbon group having from about 3 to about 10 members.

A, A', D, D', $T_n$, $T'_n$, $W_m$, $W'_m$, Y, Y' and X include sufficient additional bonds to adjacent atoms to lead to stable molecules. Segments 1 and 2 represent independent parts of the structure and the Structure I may be symmetrical or unsymmetrical so that the two sections 1 and 2 may comprise the same or different atoms. Compounds having Structure I form stable complexes with cations.

In another aspect of the invention, compounds comprising Structure II form stable complexes with cations.

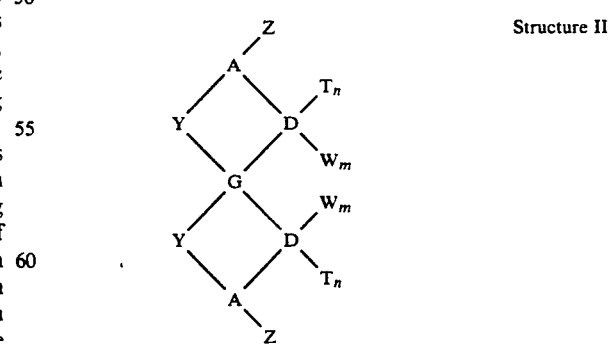

Structure II wherein: A, D, G, T, W, R, m, n and Y are defined in Structure I, and Z independently represents a hydrocarbon or heterocarbon radical having at least two members.

Advantageously, the complexing agents of the invention are capable of selectively binding with lithium ions without interference from other cations. The unique design of the molecules allows a choice of various predetermined molecular substituents which can be selected to modify the molecule to allow binding with a particular cation.

DETAILED DESCRIPTION OF THE INVENTION

Structures I and II comprise the nucleus of atoms of the complexing agents of the present invention. Each atom indicated in the structures possesses a sufficient number of bonds either to adjacent atoms or to other atoms not shown to form stable compounds. The basic molecules of the invention consist of the atoms shown in Structures I and II and as many additional hydrogen or other atoms to render the molecule stable. Any other atoms are possible, although they usually are carbon, oxygen, nitrogen, sulfur, phosphorus, fluorine, chlorine, bromine or iodine. These additional atoms may constitute any organic or inorganic moiety. Some suitable inorganic moieties include, for example, halo, a nitrogen oxide such as nitro, a sulfur oxide such as $SO_3H$, amino and the like.

Suitable organic moieties include, for example, alkyl, aryl, alkylaryl, arylalkyl and substituted amino. The alkyl groups may be branched or unbranched, cyclic or acyclic, and are preferably from 1–30 carbon atoms, preferably 2–20 carbon atoms, and more preferably 3–6 carbon atoms. The alkyl group may be fully saturated or may contain one or more multiple bonds. The carbon atoms of the alkyl group may be continuous or may be separated by one or more functional groups, such as an oxygen atom, a keto group, an amino group, an amido group, an oxycarbonyl group, and the like. The alkyl group may also be substituted with one or more aryl groups as disclosed below. Cyclic organic moieties may be aromatic or non-aromatic, and may be fused to other rings, such as to any of the rings shown in Structures I and II.

The aryl group may, for example, be a phenyl group, which may be unsubstituted or substituted with any of the inorganic or organic groups discussed above. The aryl group may also be a heteroaryl group, containing one or more ring oxygen, nitrogen or sulfur atoms; be five, six or seven membered; and be fused to other saturated or unsaturated rings.

The amino group may be substituted by, for example, any alkyl or aryl group discussed above.

Other substituents added to the molecules of the present invention may be rings or atoms, or may form additional rings fused to the nucleus of rings shown in structures I and II.

Important aspects of the claimed molecules are that they have D, D', $W_m$, $W'_m$, $T_n$, $T'_n$, Y, Y' and X or Z in the positions shown and the X or Z groups help to maintain the desired size, shape and stability of the molecular cavity. Y and Y' are important in maintaining the arrangement of polar groups which act as binding sites for cations. Another important aspect of the invention is that the claimed molecules have sufficient sites to selectively bind to the desired ions. These sites can include, for example, ether oxygen, C=O, N=N—O, C=N, —S—, S=O,

C=O, N=N—O, C=N, —S—, S=O,

-continued

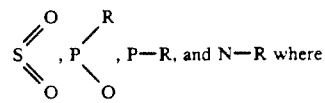

P—R, and N—R where R=alkyl, aryl or OR'. The binding sites are preferably ether, ketone or amide oxygen atoms or more preferably piperidone rings. It is to be noted than in piperidone rings the binding sites are amide oxygen atoms.

A binding portion of the molecule, represented by

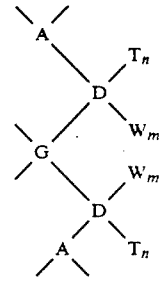

may be, for example:

i   ii   iii iv   v   vi   vii

R = alkyl, aryl, or OR' viii   ix   x

-continued

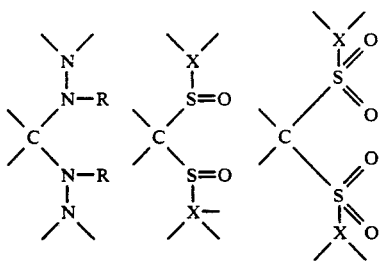

X = CH or N
R = same as above

Y and Y' (hereinafter "(Y)") may comprise a hydrocarbon radical with or without hetero substituents, having from 1 to about 10 members. (Y) may include members of atoms having a valence number from 2 to 6, for example, carbon, nitrogen, oxygen, sulfur and phosphorus. When oxygen, sulfur, nitrogen or phosphorus are present as members in (Y), the number of these atoms may be 1 or 2. If two atoms of sulfur, oxygen, or phosphorous are present as members in (Y), they are not adjacent to each other. (Y) may comprise a chain or a ring structure which may be aromatic or heterocyclic with a fused ring or rings having members as described above for Y and Y'. (Y) is preferably bonded to A through a carbon member of (Y) including through a keto-carbon. (Y) may be, for example $(CH_2)_n$ where $n=1$ to about 10, preferably $n=1$ to about 4. (Y) may also be, for example, as shown below in structures xiv to xxvi which also show amide binding sites. Structures xiv to xxiv are examples which represent section 1 and/or section 2 of Structure I.

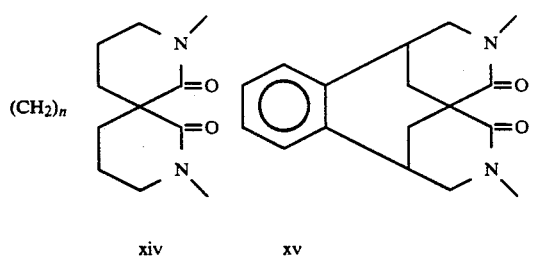

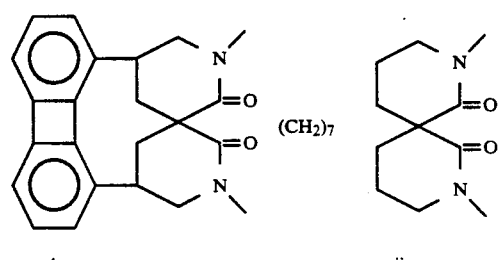

-continued

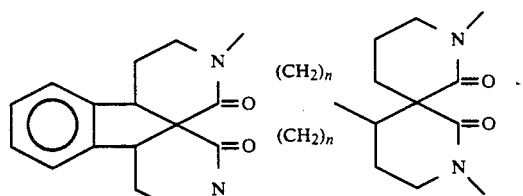

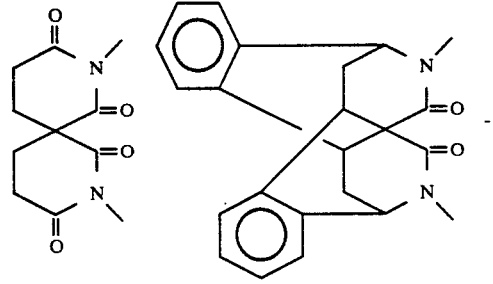

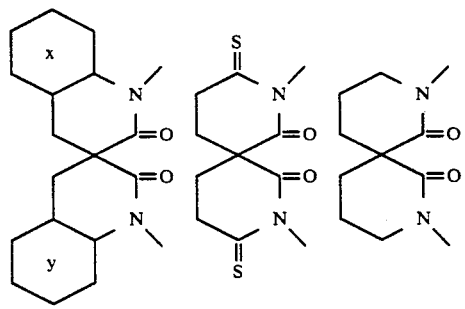

rings x and y
can be aromatic
or saturated

In addition, piperidene rings useful in the invention may be modified to comprise the following:

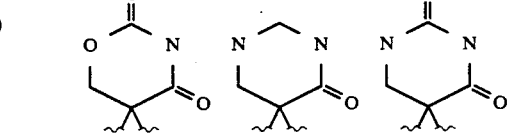

X represents groups which are bulky substituents. For the purposes of this Specification, the term "bulky substituents" is intended to mean groups which are large enough to hinder or block the approach of another compound which would prevent or disfavor the formation of complexes of the structures of the invention with cations. These substituents may be used to vary the stoichiometry of the complexes and thereby the size and shape of the molecular cavities. It is preferred that X does not hinder the molecular cavity itself and it preferably extends horizontally between the two segments of the molecule. X may comprise a bridge radical having from about 3 to about 10 members when counted linearly. X may comprise a chain, aromatic ring, or fused ring or rings having members of carbon, oxygen, sulfur, nitrogen and phosphorus. The members are preferably carbon atoms. The bulky groups of X may comprise, for example, phenyl, dialkylphenyl, anthracenyl, acetylenic, diacetylenic groups; also suitable are naphthalene, phenanthrene, pyrene, bicyclo[2.2.2]octane, and tryptycene. These groups are preferably connected to A and A' through a (CH$_2$) group.

Some specific examples of the bulky substituents represented by X are as shown in structures a through p:

n = 0 to 4

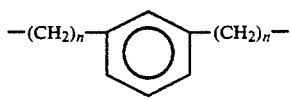
a

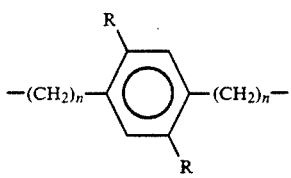
b

R = H, alkyl or aryl

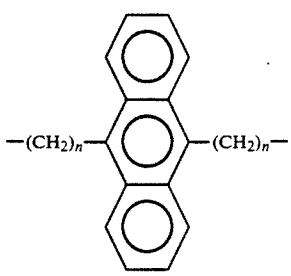
c

d

e

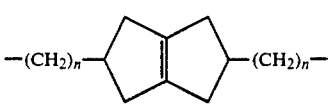
f

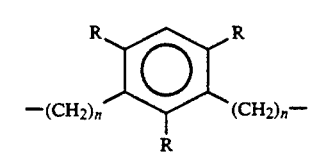
g

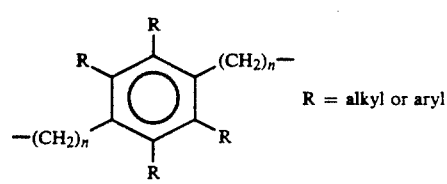
h

R = alkyl or aryl

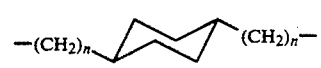
i

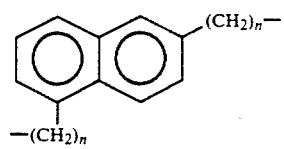
j

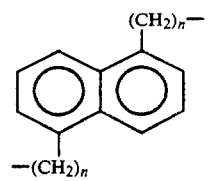
k

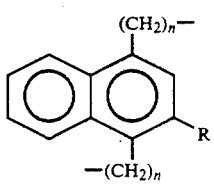
l

R = alkyl or aryl

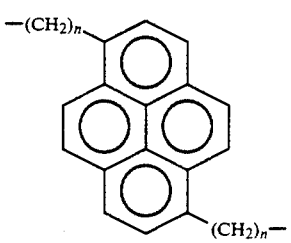
m

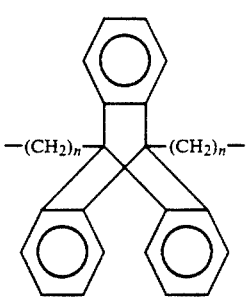
n

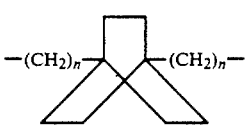
o

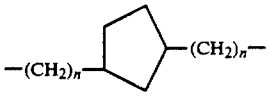
p

A more specific example of some of the molecules encompassed by Structure I is shown as Structure A:

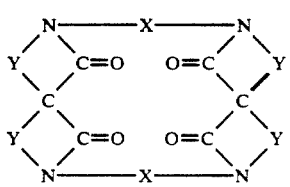

wherein:
C represents carbon atoms;
N represents nitrogen atoms;
O represents oxygen atoms;
Y is a hydrocarbon or heterocarbon radical having from 1 to about 10 members;
X is a hydrocarbon or heterocarbon radical having from about 3 to about 10 linear members.

In one embodiment, Structure A may be as shown in compound 10:

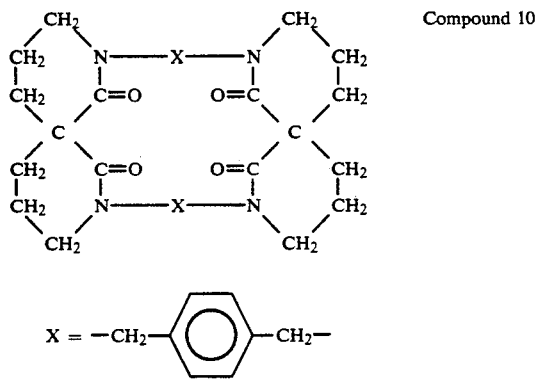

Compound 10

X = Rigid groups of variable length and bulkiness

Compound 10 will be called the spiromacrocycle.

Structure II can be used independently to form stable complexes with cations, selectively complexing with ions when Z is a radical having at least two linear members. Z comprises a bulky group, preferably has from 2 to 10 members counted linearly, and preferably has a branched alpha carbon. Z can include chains and saturated or aromatic fused or unfused rings and can be carbocyclic or heterocyclic. Z may also include additional binding sites. When the molecule is used to complex Li+, Z preferably has no binding sites. The term "counted linearly" is intended to mean for example, if Z is a phenyl group:

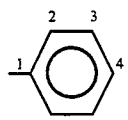

the length of the radical is counted as indicated for a total of 4 members. Z may be, for example —CH$_2$Ph, —CHPh$_2$,—CPh$_3$,-t-butyl, neopentyl, bicyclo[2.2.2]oct-1-yl, bicyclo[2.2.1]hept-1-yl, and tryptycyl.

Compound 9 is a known form of Structure II when Z=H.

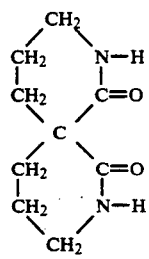

Compound 9

Compound 9 is 2,8-Diazaspiro[5,5]undecane-1,7-dione which will be called the spirodiamide. The spirodiamide is an intermediate in the production of the compound represented by formula 10 and may be made from diethyl malonate and 3-amino-1-propanol or acrylonitrile. The dianion of the compound represented by formula 9 is alkylated with the desired alkyl chloride, bromide or iodide to form Structure II. Compound 10 may be made by high dilution macrocyclization of the dianion of 9 with a dihalide (e.g. Cl—Y—Cl) or by a stepwise procedure.

The invention also includes stable complexes of cations with the complexing agents described herein. Ions which may be complexed include the metals of Groups IA and IIA of the Periodic Table, for example lithium, sodium, potassium, rubidium, cesium, beryllium, magnesium, calcium, strontium and barium, and also ammonium ions. The number of binding site ligands, the bulky groups of X or Z and the ratio of complexing molecules to cations may be varied depending upon the selectivity desired. In one preferred embodiment of a Structure I complex, when Li+ is complexed, the ratio of complexed ion to complexing molecule is 1:1. In one preferred embodiment of a complex with Structure II, the ratio of complexed ion to complexing molecule is 1:2. This ratio may vary depending on the number of binding sites and which cation is complexed. Stable compounds are those with appreciable lifetimes at room temperature.

The molecule of Structure A may form a stable complex with a cation as shown, for example, by Structure B:

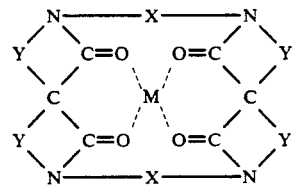

wherein:
C, N, O, Y and X are as in Structure A and M is a complexed cation.

A more specific example of some of the molecules encompassed by Structure II and complexed with a cation is shown, for example, by Structure C:

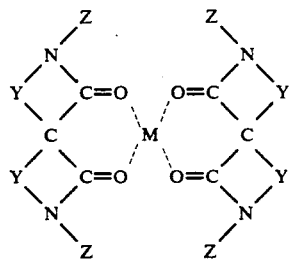

wherein:
C, N, O, Y and M are as in formula B; and Z is a hydrocarbon or heterocarbon radical having at least two members.

As indicated above, the molecules of the invention may be used as ionophores to selectively complex with cations. The selective ability can be used, for example, to measure the amount of lithium, potassium or sodium in a sample such as from bodily fluids. Using the invention, selectivity for Li+ is possible even against a high background of potentially interfering ions such as K+ and Na+. Selectivity is the tendency for a compound, also called an ionophore, to complex with a certain ion in preference to other ions. Generally, the compounds of the invention are more selective for a smaller ion relative to a larger ion. The size of the molecular cavity and the number of binding site ligands can be varied for the desired selectivity.

Methods for determining the amount of metal ions in a sample include the use of an ion selective electrode (ISE). The term ISE is generally applied to a membrane electrode which responds selectively toward an ion species in the presence of other ions. The term membrane denotes a thin section of electrically conducting material separating two solutions across which a potential develops at the membrane interface. A rapid ion-exchange process takes place between the free ions in solution and the same ions bound to the organic site groups of complexing molecules. The selectivity of the electrode depends primarily on the selectivity of the ion-exchange process. An ionophore is impregnated into the membrane and the particular ionophore used endows the membrane with its selectivity.

The compounds of the present invention may be prepared by modifications of methods generally known in the art. The synthesis of compounds 9, 10, 11, 12 and 13 will be used for illustrative purposes. Further modifications of the illustrative reactions will be apparent to those skilled in the art for making other compounds of the invention.

An important intermediate in the synthesis of compounds 10, 11, 12 and 13 is 2,8-diazaspiro[5,5]undecane-1,7-dione (9) which may be prepared by cyanoethylation of diethyl malonate in dioxane in the presence of a catalytic amount of trimethylbenzyl ammonium hydroxide ("Triton B") at room temperature followed by reduction of the crude bis(2-cyanoethyl)malonate in ethanol with Raney nickel catalyst in a medium pressure hydrogenator (40 psi). This gives compound 9 (m.p. 327°-330°), the spirodiamide, in 60% yield after recrystallization from water. Compound 9 has very low solubility in most organic solvents, is sparingly soluble in dimethylformamide, and moderately soluble in warm dimethyl sulfoxide.

Because of this limited solubility, a sodium salt of the product is prepared using sodium methylsulfinylcarbanion in dimethyl sulfoxide. Benzyl chloride can be used for alkylation of the sodium salt to form N,N'-bisbenzyl spirodiamide which is compound 11. Bulkier derivatives such as the N,N'-bis(diphenylmethyl) spirodiamide (compound 12) and the N,N'-bis(9-anthracenylmethyl) spirodiamide (compound 13) can be synthesized with diphenylmethyl chloride and 9-anthracenylmethyl chloride, respectively. Similar methods may be used to form other derivatives.

The compound 9 spirodiamide can be cyclized to form compound 10, the spiromacrocycle. This cyclization can be carried out by first mixing the disodium salt of the spirodiamide and α,α'-dichloro-p-xylene in DMSO and heating to form the spiromacrocycle product, compound 10. Alternatively the dichloroalkylated spirodiamide may be cyclized with the spirodiamide to form compound 10.

EXAMPLES

1. Synthesis of spirodiamide (9)

Diethyl bis(2-cyanoethyl)malonate

To a solution of diethyl malonate (81 g) in 100 g of 1,4-dioxane containing Triton B (10g of 40% methanol solution) was added dropwise acrylonitrile (55 g) in a period of 30 minutes. The reaction is highly exothermic, and the temperature was controlled at 30°-40° C. by means of a water bath. The reaction mixture was stirred overnight, and later poured into 600 ml of ice-water containing hydrochloric acid (5 ml of conc. HCl). The white precipitate formed was collected by filtration and washed with water. The crude product (m.p. 61°-63° C., 100% yield) was used for the next step without further purification.

$^1$H NMR (300 MHz, CDCl$_3$) δ 4.24 (q, J=7.1 Hz, 4H), 2.44 (t, J=7.7 Hz, 4H), 2.23 (t, J=7.7 Hz, 4H), 1.27 (t, J=7.1 Hz, 6H); $^{13}$C NMR (75 MHz, CDCl$_3$) δ 168.98 (C=O), 118.36 (C≡N), 62.29(O—CH$_2$—), 55.58 (O=C—C—C=O), 29.55 (C—C—C—N), 13.78 (C—C≡N), 12.95 (—CH$_3$); IR (film) 2995 s, 2950 m, 2250 s, 1745 s, 1725 s, 1450, 1370, 1200, 1100, 1025(cm$^{-1}$)

2,8-Diazaspiro[5,5]undecane-1,7-dione

To a solution of diethyl bis(2-cyanoethyl)malonate (13.4 g) in 150 ml of ethanol was added 5 g of Raney nickel (washed with ethanol). The Raney nickel slurry was washed down with an extra 50 ml of ethanol. After setting up the reaction bottle under hydrogen (40 psi), the hydrogenation reaction bottle was wrapped with a heating coil and heated to 80° C. using a variable transformer. The resulting heterogeneous reaction mixture was stirred vigorously with magnetic stirring under hydrogen for 45 hours. After the solvent was removed in vacuo, the reaction mixture was boiled in water and the aqueous mixture was hot-filtered to remove the nickel catalyst. On concentrating and cooling the filtrate, white crystals which formed were collected by filtration and washed with acetone. The crude product (5.45 g, 60%) was recrystallized from boiling water.

m.p. (from water); 327°-330° C.; $^1$H NMR (300 MHz,D$_2$O) δ7.4 (b,2H in DMSO-d$_6$), 3.15(m,4H), 2.05 (m,2H), 1.95 (m,2H), 1.80(m,4H); $^{13}$C NMR (75 MHz,D$_2$O) δ 175.23, 50.20, 41.87, 30.9, 17.6; MASS (m/e) 183 (M+1, 4.7) 182 (M+1, 38), 181 (M-1, 3.3), 154 (8.3), 112 (100%); IR (KBr) 3350-3700 b, 3280 br. s, 3200 br. s, 3070 br. s, 2950 s, 2880 m, 1670 s, 1640 s, 1485 s, 1450 m, 1400 s, 1350 s, 1315 s, 1285 m, 1210 s, 1200 m, 1125 m, 1030 m, 980 m, 940 m, 905 m, 875 m, 830 br. s, 650 m, 610 m, 500 s, 450 m(cm$^{-1}$).

Scheme 1.
Synthesis of 2,8-diazaspiro[5,5] undecane-1,7-dione (9).

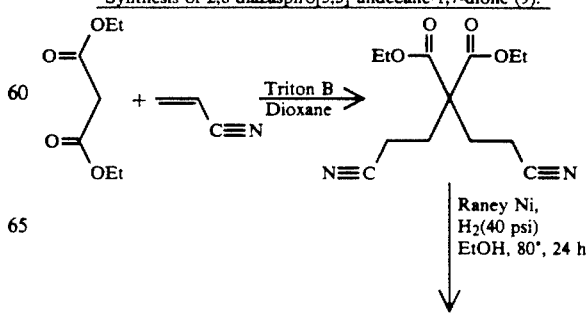

Scheme 1.
Synthesis of 2,8-diazaspiro[5.5]undecane-1,7-dione (9).

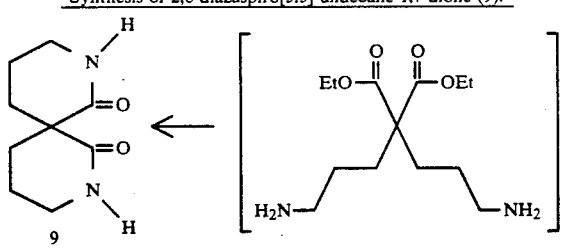

Scheme 2.
Macrocyclization by slow addition method

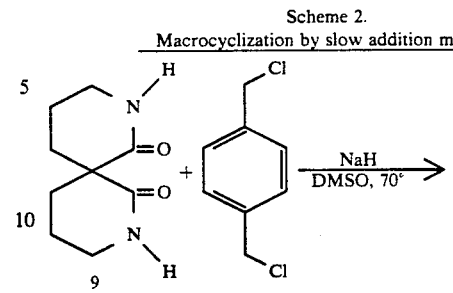

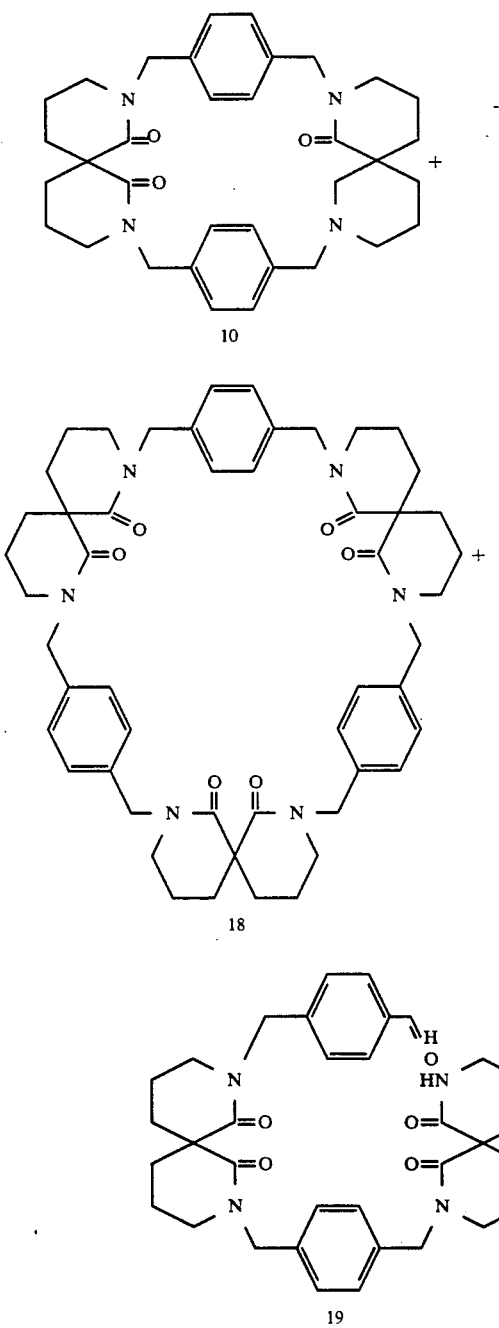

2 Synthesis of spiromacrocycle (10)

METHOD 1: Direct cyclization reaction of spirodiamide 9 with α,α'-dichloro-p-xylene by slow addition method Sodium methylsulfinylcarbanion in DMSO was prepared by the same method as described for compound 11 with sodium hydride (180 mg of 60% dispersion) and DMSO (20 ml) at 65° C. To a clear solution was added spirodiamide (364 mg) and the reaction mixture was stirred for 30 minutes. The spirodiamide dianion solution was transferred to a 50 ml syringe and diluted to 35 ml with extra DMSO. A solution of α,α'-di-chloro-p-xylene (350 mg) in DMSO was prepared in a 10 ml syringe. The two solutions were simultaneously added dropwise by a syringe pump over a period of 2 hours to a mixture of MgSO$_4$ (480 mg) in 250 ml of anhydrous DMSO heated at 70° C. using an oil bath. The reaction mixture was heated at 70° C. for an additional 2 hours. The DMSO was removed by vacuum distillation at a pot temperature of approx. 100° C. The yellowish residue was dissolved in chloroform (100 ml) and brine (100 ml) was added to the chloroform solution. The chloroform layer was withdrawn and the aqueous layer was further extracted with chloroform (3×100 ml). The combined chloroform solutions were dried over MgSO$_4$ and concentrated in vacuo. The residue (870 mg) was loaded on a chromatography column (flash silica gel), and eluted with 20% MeOH in ethyl acetate. Two products were isolated, a yellowish oil (110 mg, 19%, R$_f$=0.47 silica gel, MeOH-ethyl acetate (1:1)) and fluffy powder (106 mg, 19%, R$_f$=0.38). The oily product was found to be mainly a (2+2) spiromacrocycle 10 but it was contaminated with the corresponding aldehyde (19). The solid product was characterized as the (3+3) spiromacrocycle and was also contaminated with some polymeric by-products. The solid product was further purified by preparative TLC (silica gel, MeOH-ethylacetate (1:1)).

(2+2) Spiromacrocycle 10 yield: 27 mg (7%); m.p.=324°-326° C.;

R$_f$(silica gel, ethyl acetate)=0.11;

$^1$H NMR (300 MHz, CDCl$_3$) δ 7.21 (s, 8 H), 5.44 (d, J=14.7 Hz, 4 H), 3.41 (d, J=14.7 Hz, 4 H), 3.6 (m, 4 H), 3.3 (m, 4 H), 2.4 (m, 8 H) 1.7 (m, 8 H); 13C NMR (75 MHz, CDCl$_3$) δ 170.22, 135.86, 127.78, 51.93, 48.59, 48.53, 33.92, 20.51; IR (film) 2930 s, 2860 m, 2358 m, 1627 s, 1513 m, 1484 m, 1440 m, 1416 m, 1349 m, 1285 m, 1204 m, 1172 m, 967 W, 728 m (cm$^{-1}$); MASS (FAB) 568 (M+, 11%), 569 (100%), 586 (M+18, 58%), 587 (24%), 285 (36.6%), 284 (M/2, 13.1%), 182 (7.2%), 181 (6.4%).

METHOD 2: Cyclization reaction of N,N'-bis-p-chloromethylphenylmethyl)-2,8-diazaspiro-[5,5]undecane-1,7-dione N,N'-Bis(p-chloromethylphenylmethyl)-2,8-diazaspiro[5,5]undecane-1,7-dione (15): Sodium methylsulfinylcarbanion in DMSO was prepared as in method 1 with sodium hydride (185 mg of 60% dispersion) and DMSO (30 ml) at 65° C. To a clear solution was added spirodiamide (364 mg) and this reaction mixture was stirred for 30 minutes. To tis spirodiamide dianion solution a solution of α,α'-dichloro-p-xylene in DMSO (1.05 g/10 ml) was added and this reaction mixture was stirred for 10 min. Brine (150 ml) was added to reaction mixture and products were extracted with chloroform. The chloroform layer was separated, dried over MgSO$_4$ and concentrated in vacuo. The product was isolated by column chromatography (fresh silica gel, hexane-ethyl acetate (1:1)).

yield: 332 mg (36%);

$R_f$(ethyl acetate, silica gel)=0.37;

$^1$H NMR (300 MHz, CDCl$_3$) δ 7.32 (d, J=8.1 Hz, 4 H), 7.26 (d, J=8.1 Hz, 4 H), 4.74 (d, J=14 Hz, 2 H), 4.56 (d, J=14, Hz, 2 H), 4.53 (s, 4 H), 3.4 (m, 2 H), 3.2 (m, 2 H), 2.5 (m, 2 H), 2.0 (m, 2 H), 1.8 (m, 4 H); $^{13}$C NMR (75 MHz, CDCl$_3$) δ 171.22, 137.45, 136.33, 128.81, 128.00, 50.99, 50.30, 47.38, 45.94, 32.86, 19.25; IR (film) 3010 w, 3030 w, 3060 w, 2940 m, 2870 m, 1625 s, 1515 m, 1485 m, 1460 m, 1440 m, 1420 m, 1350 m, 1270 m, 1195 m, 725 m, 675 m (cm$^{-1}$).

A mixture of spirodiamide (160 mg) and NaH (90 mg of 60% oil dispersion washed with hexane) was dissolved in 300 ml DMSO under nitrogen. The reaction mixture was heated for 40 min. at 60°-65° C. To this spirodiamide dianion solution a solution of N,N'-bis(p-chloromethylphenylmethyl)-2,8-diazaspiro[5,5]undecane-1,7-dione in DMSO (332 mg/25 ml) was added slowly by a syringe pump over 30 min. Just after addition was complete, the solvent was removed by vacuum distillation (0.5 mm, 95° C. oil bath temperature). The reaction residue was dissolved in chloroform. The chloroform solution was washed with water, dried over MgSO$_4$ and concentrated in vacuo. Two products were isolated by column chromatography (fresh silica gel, ethyl acetate to ethyl acetate-methanol (1:1)).

(2+2) Spiromacrocycle (10) spectral data are in method 1.

3. Modification of compound 9

N-Alkylation of 2,8-diazaspiro[5,5]undecane-1,7-dione

Because of limited solubility of spirodiamide 9 in organic solvents, Fones's method (Ogawa et al., *Am. Chem. Soc.* 1984, 106, 5760–5762) using sodium hydride in xylene was modified to form a sodium salt of spirodiamide 9.

Scheme 3.
N-Alkylation of spirodiamide.

-continued
Scheme 3.
N-Alkylation of spirodiamide.

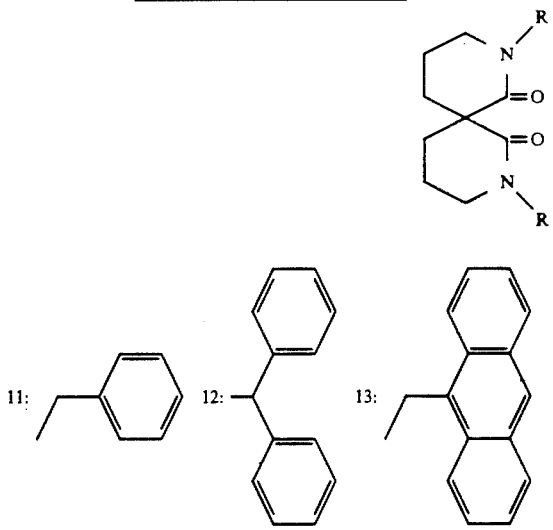

N,N'-Bisbenzyl spirodiamide 11 was obtained by diethyl ether extraction from the brine-DMSO reaction mixture in 80–93% yield. Bulkier derivatives N,N'-bis(diphenylmethyl)-spirodiamide 12 and N,N'-bis(9-anthracenylmethyl)-spirodiamide 13 have also been synthesized from diphenymethyl chloride and 9-anthracenylmethyl chloride, respectively. N,N'-bis(9-anthracenylmethyl)spirodiamide 13 was synthesized using the same method as bisbenzyl derivative 11 and isolated by column chromatography in 35% yield. The anthracenyl group in 13 is sensitive to oxygen, so analytically pure crystalline product was collected directly from fractions by cooling the chromatography fractions in a refrigerator under nitrogen. Diphenylmethyl chloride itself reacted with the basic equilibrium mixture of sodium methylsulfinylcarbanion and spirodiamide dianion in DMSO to produce a fluorescent product, tetraphenylethene. By employing a 100% excess of diphenylmethyl chloride, N,N'-bis(diphenylmethyl)-spirodiamide 12 was isolated by column chromatography in 22% yield.

A Compound 11

N,N'-Bisbenzyl-2,8-Diazaspiro[5,5]undecane-1,7-dione (11)

Sodium methylsulfinylcarbanion in DMSO was prepared from the reaction of powered sodium hydride (900 mg washed with hexane) with freshly distilled DMSO (50 ml) at 70° C. for 40 minutes under nitrogen with stirring until evolution of hydrogen was completed. To the clear solution was added dry solid spirodiamide (1.82 g) and the reaction mixture was stirred for 30 minutes to form a viscous solution. To the solution of the dianion, benzyl chloride (2.66 g) was ¹H NMR (300 MHz, CDCl₃) δ 7.3 (m, 10 H), 4.74 (d, J=14.9 Hz, 2 H), 4.56 (d, J=14.9 Hz, 2 H), 3.37 (m, 2 H), 3.21 (m, 2 H), 2.50 (m, 2 H), 2.00 (m, 2 H), 1.81 (m, 4 H); ¹³C NMR (75 MHz, CDCl₃) δ 171.19, 137.12, 128.49, 127.67, 127.05, 51.01, 50.58, 47.25, 33.01, 19.33; IR (KBr) 3059 w, 3026 w, 2938 m, 2866 W, 1625 s, 1486 m, 1452 m, 1431 m, 1350 m, 1333 W, 1284 W, 1195 m, 732 m (cm⁻¹); MASS (m/e) 362 (1.4), 271 (4.1), 186 (12.7), 181 (1.4), 133 (22.3), 132 (17.7), 91 (100%): Analysis calculated for C₂₃H₂₆N₂O₂; C 76.21%, H 7.23%, N 7.73%; Found C 76.45%, H 7.28%, N 7.74%.

The chemical shifts for 11 were assigned as follows from the results of 2D NMR experiments (CSCM and COSY):

¹³C NMR; C₁:171.19, C₃:47.25, C₄:33.01, C₅:19.32, C₆:51.01, C_{benzylic}:50.58, Ar. C_i:137.12, C_o:128.49, C_m:127.67, C_p:127.05.

¹H NMR; H₃ₑ:3.21, H₃ₐ:3.37, H₄ₑ:2.50, H₄ₐ:1.81, H₅:1.81 and 2.00, Hₐ and H_b:4.56 and 4.74.

N,N'-Bisbenzyl-2,8-diazaspiro[5,5]undecane-1,7-dione 11 and N-benzyl-2,8-diazaspiro[5,5]undecane-1,7-dione from reaction in toluene (Fones, *J. Org. Chem.* 1949, 14, 1099–1102).

Spirodiamide 9 (910 mg) and NaH (200 mg of 60% dispersion in oil) were mixed in 250 ml of xylene, and the reaction mixture was refluxed under nitrogen for 24 hours. To the refluxing diamide solution a 3-fold excess of benzyl chloride (3.78 g) was added and the reflux was continued for an additional 15 hours. After cooling, the unreacted spirodiamide (9) was recovered by filtration. The filtrate was concentrated in vacuo and the residue was loaded onto a flash silica gel column. The products were isolated by eluting with 50–100% ethyl acetate in hexane. Dialkylated product 11 (470 mg) and the following monoalkylated products (493 mg) were isolated.

Physical data for N-benzyl-2,8-Diazaspiro[5,5]undecane-1,7-dione; oil; IH NMR (300 MHz, CDCl₃) δ 7.3 (m, 5 H), 6.3 (br, 1 H), 4.69 (d, J=14.8 Hz, 1 H), 4.50 (d, J=14.8 Hz, 1 H), 3.5 (m, 1 H), 3.3 (m, 2 H), 3.18 (m, 1 H), 2.42 (m, 2 H), 2.0 (m, 2 H), 1.8 (m, 4 H); ¹³C NMR (75 MHz, CDCl₃) δ 173.09, 170.88, 137.04, 128.44, 127.68, 127.09, 50.56 (benzylic), 50.41, 47.23, 42.25, 32.51, 19.07, 18.91; IR (film) 3200–3600 br, 3060, 3030, 2940, 2870, 1660, 1630, 1485, 1495, 1450, 1350, 1210, 735, 700 (cm⁻¹).

B. Compound 12

N,N'-Bis(diphenylmethyl)-2,8-diazaspiro[5,5]undecane-1,7-dione (12)

Sodium methylsulfinylcarbanion in DMSO was prepared by the same method as described for compound 11, using sodium hydride (90 mg of 60% dispersion) and DMSO (5 ml) at 60° C. To the clear solution was added spirodiamide 9 (182 mg) and the reaction mixture was stirred for 30 minutes. An excess (100%) of diphenyl methyl chloride (810 mg) was added and the reaction mixture was further stirred for an additional 4 hours at 60°–65° C. The work-up employed was similar to that described for compound 11. The reaction mixture was separated by column chromatography (flash silica gel, CH₂Cl₂-CHCl₃). Bis-alkylated product (116 mg, 22%) was isolated and was recrystallized from ethyl acetate (m.p. 168°–169° C.). A mono-alkylated product (57 mg, 16%, m.p. 198.5°–200° C.) was obtained by filtration of the of the ether extract.

¹H NMR (300 MHz, CDCl₃) δ 7.3 (m, 20 H), 5.75 (s, 2 H), 3.10 (m, 2 H), 3.00 (m, 2 H), 2.45 (m, 2 H), 2.05 (m, 2 H), 1.80 (m, 4 H); ¹³C NMR (75 MHz, CDCl₃) δ 171.47, 144.03, 138.79, 136.19, 129.02, 128.43, 128.33, 128.27, 127.22, 127.10, 126.40, 60.11, 51.84, 44.43, 33.48, 19.59; IR (KBr) 3059 w, 3027 w, 2938 m, 2873 W, 1622 s, 1494, 1453, 1427, 1301, 1185, 911, 759, 732 s, 701 s, 575 (cm⁻¹); Analysis calculated for C₃₅H₃₄N₂O₂; C 81.68%, H 6.66%, N 5.44%; Found C 81.57%, H 6.72%, N 5.41%.

N-Diphenylmethyl-2,8-diazaspiro[5,5]undecane-1,7-dione

This product was isolated from the above reaction employed for the synthesis of 12.

m.p. 198.5°–200.0° C.; ¹H NMR (300 MHz, CDCl₃) δ 7.3 (m, 10 H), 5.8 (b, 1 H), 3.50 (m, 1 H), 3.33 (m, 1 H), 3.13 (m, 1 H), 3.00 (m, 1 H), 2.55 (m, 1 H), 2.40 (m, 1 H), 2.12 (m, 1 H), 2.02 (m, 1 H), 1.80 (m, 4 H); ¹³C NMR (75 MHz, CDCl₃) δ 173.07, 170.95, 138.84, 138.22, 128.95, 128.80, 128.36, 127.36, 127.14, 60.35, 50.83, 44.40, 42.40, 33.02, 32.87, 19.55, 18.99; IR (KBr) 3300 b, 3061 w, 2939 m, 2872 w, 1663 s, 1627 s, 1493 m, 1453 m, 1432 m, 1348 m, 1303 m, 733 m, 702 m (cm⁻¹).

C. Compound 13

N,N'-Bis(9-anthracenylmethyl)-2,8-diazaspiro[5,5]undecane-1,7-dione (13)

Sodium methylsulfinylcarbanion in DMSO was prepared by the same method as described for compound 11 using sodium hydride (90 mg of 60% dispersion) and DMSO (5 ml) at 65° C. To the clear solution was added spirodiamide (182 mg) and the reaction mixture was stirred for 30 minutes. Then 9-(chloromethyl)anthracene (454 mg) was added to this solution and the reaction mixture was stirred for an additional 4 hours at 65° C. When brine was added to the reaction mixture a precipitate was formed. This precipitate was collected by filtration and dissolved in a minimum amount of chloroform. The product was isolated by column chromatography of the chloroform solution (flash silica gel, CH₂Cl₂, then 30% ethyl acetate in hexane). A product (200 mg) was obtained but it was unstable on contact with air. The pure product could be obtained by recrystallization from methylene chloride under nitrogen. The product was repurified by chromatography. It was crystallized from the chromatography fractions and collected by filtration under nitrogen.

m.p. 293°–294° C.; ¹H NMR (300 MHz, CDCl₃) δ 8.45 (s, 2 H), 8.37 (d, J=8.7 Hz, 4 H), 8.01 (d, J=8.3 Hz, 4H), 7.56 (t, J=7.5 Hz, 4H), 7.47 (t, J=7.4 Hz, 4 H) 6.18 (d, J=15.0 Hz, 2 H), 5.42 (d, J=15.0 Hz, 2 H), 3.22 (m, 2 H) 2.77 (m, 2 H), 2.44 (m, 2 H), 1.77 (m, 2 H), 1.56 (m, 2 H), 1.43 (m, 2 H); ¹³C NMR (75 MHz, CDCl₃) δ 170.93, 131.39, 131.31, 129.13, 128.14, 127.76, 126.45, 125.08, 124.29, 51.94, 45.53, 41.48, 32.78, 19.15; IR (KBr) 3050 w, 2940 m, 2866 w, 1618 s, 1523 m, 1484 m, 1447 m, 1435 m, 1349 m, 1337 m, 1316 m, 1252 m, 1184 m, 736 s (cm⁻¹); MASS (m/e) 372 (2.8), 371 (M-191, 10.1), 192 (17.8), 191 (100), 181 (0.2), 180 (0.5%); UV & VIS (in CH₃CN) ε_{max}=22,330 at λ_{max}=366.5 nm, ε=22,000 at λ=386.4 nm, ε=14,200 at λ=348.4 nm, ε=6,600 at λ=332.8 nm; Analysis calculated for C₃₉H₃₄N₂O₂; C 83.24%, H 6.09%, N 4.98%; Found C 83.11%, H 5.76%, N 4.78%.

The compounds synthesized above were tested for ion selectivity.

4. Li+ Selectivities toward alkali and alkaline earth metal ions

Ion-selective electrode membranes

Selectivities for a given ionophore vary depending on the exact membrane composition, the composition of solution to which the membrane is exposed, and the method of measurement used for calculating the selectivity coefficient. The incorporation of salts of lipophilic anions such potassium tetrakis(p-chlorophenyl)-borate (KTpClPB) into the membrane phase reduces the interference by sample anions. In the past it has been observed that some ligands behave as ionophores only in the presence of such lipophilic anionic sites. Selectivities for a given ionophore are very sensitive to the amount of such lipophilic anions relative to the ligand concentration.

In view of the above factors, all ionophores were treated in the same PVC membranes and the same plasticizer in order to obtain relative responses due to ionophores. Simon's method (Simon et al., *Anal. Chem.* 1987, 59, 1600–1603) was employed.

Electromotive force measurement

Reagents and Chemicals. High molecular weight poly(vinyl chloride) (PVC), potassium tetrakis(p-chlorophenyl)borate (KTpClPB), and the plasticizer, o-nitrophenyloctyl ether (o-NPOE) were obtained from Fluka AG for ion-selective electrodes. All solutions (0.1M aqueous) were prepared from salts of reagent grade using twice distilled water. The chloride salts of the metals were used in all cases. Neutral carriers were prepared in the laboratory. The syntheses of spiro-based carriers were described above.

Electrode System: Measurements were carried out by the use of the following cell:

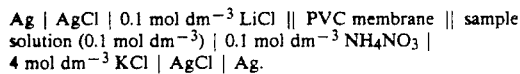

A Corning pH/ion meter 150 was used in monitoring the voltage and all data were printed out on a Corning thermal printer.

PVC-Plasticizer Stock Solution

Stock solutions were prepared for membranes which, including one membrane for a control experiment without carrier and membranes for different added carriers. PVC (356 mg, 33 wt-%) and KTpClPB (4.5 mg, $1.5 \times 10^{-4}$ mMol per membrane) were mixed with 713 mg of o-NPOE plasticizer. Anhydrous THF was added to the mixture, which was stirred to dissolve thoroughly and the solution volume was adjusted to a total of 9 ml. To individual neutral carriers ($5 \times 10^{-3}$ mmol for 1:2 complex ligands and $2.5 \times 10^{-3}$ mmol for 1:1 complex ligands) was added 1.5 ml of this stock solution. This corresponds to a 1–1.4 wt.-% of neutral carrier in each membrane.

Membrane preparation 1.5 ml of the above THF solution was transferred into a glass ring (1" i.d.) which rested on a glass plate. After solvent evaporation in a closed cardboard box overnight, the resulting membrane was peeled away from the glass.

Ion-Selective Electrode Construction

A membrane disk of 10 mm diameter was cut by using a scalpel or scissors and was mounted in an Orion liquid-membrane electrode body (model 92), which is designed for a paper impregnated liquid membrane. To easily mount the PVC membrane disk this electrode body was modified by placing a plastic tube on the plastic hollow cylinder that presses on the membrane. Lithium chloride (0.1M) was used as an internal filling solution.

EMF Measurement

The measurements were performed at 24 ±1° C. using an Orion ion meter and a Ag/AgCl reference electrode. The EMF readings were referenced to zero for a 0.1M - LiCl sample solution. The EMF readings for other metal ions were used directly for selectivity calculation.

|         | Control | 10     | 11    | 12    | 13    |
|---------|---------|--------|-------|-------|-------|
| Li+     | (99)    | (184)  | (91)  | (97)  | (83)  |
| Na+     | 0.37    | −1.40  | −0.04 | −0.08 | 0.40  |
| K+      | 1.97    | 0.67   | 0.91  | 1.32  | 1.81  |
| Rb+     | 2.59    | 1.29   | 1.39  | 1.98  | 2.33  |
| Cs+     | 3.24    | 1.38   | 2.00  | 2.82  | 2.89  |
| NH4+    | 1.62    | 0.91   | 0.93  | 1.32  | 1.55  |
| Mg++    | −0.48   | −1.60  | 0.08  | −0.37 | 0.37  |
| Ca++    | −0.29   | −0.83  | 0.85  | 0.09  | 0.88  |
| Sr++    | −0.01   | −0.38  | 1.46  | 0.04  | 0.95  |
| Ba++    | −0.29   | −0.79  | 1.77  | 0.09  | 1.38  |
| H+      | 0.55    | −0.87  | 1.15  | 0.49  | 0.92  |

Positive selectivity factors (log $K_{Li,M}^{pot}$ values) are obtained for electrodes that are selective for comparison ion M relative to Li, whereas negative selectivity factors indicate selectivity for Li relative to ion M. The selectivity factors listed in Table 1 for the control electrode show that PVC membranes without carriers give selective response for alkali metal ion larger than lithium and that the response increases with ionic size (Li<Na<K<Rb<Cs). The control electrode is also selective for $NH_4^+$ and $H^+$ relative to $Li^+$, but alkaline earth ions (Mg, Ca, Sr and Ba) give weaker responses than Li.

Dialkylated spirodiamide ionophores 11–13 generally decrease the control electrodes selectivity toward larger alkali metal ions, but significant lithium selectivity is only observed relative to $Mg^{2+}$ with ionophore 12.

The electrode containing (2+2)spiromacrocycle 10 on the other hand, shows good selectivity toward $Li^+$ relative to $Na^+$, an important comparison for clinical ISE applications. Good selectivity is also observed for $Li^+$ relative to $Mg^{2+}$ and significant Li selectivity is also obtained relative to the other alkaline earth ions. This new Li-selective ionophore represents the parent of a new family of spirodiamide ionophores in which desired selectivity can be tuned by systematic variation of structure.

The (2+2) spiromacrocycle (compound 10) shows high Li+/Na+ selectivity. Generally, molecules with more rigidly organized quadridentate ligands will exhibit narrower selectivity range and preferred Li+/-Na+selectivity. A high selectivity can be obtained by multidentate ligand able to assume a stable conformation which provides a cavity that snugly fits the desired cation ("Ion-Selective Electrodes in Analytical Chemistry", Vol. 1, Henry Freiser Ed., Plenum Press, New York, London 1978, Chap. 3 and references therein). The problem has been how to attain that stable conformation. The invention presents a new approach in overcoming the problem. By further modification of the spiromacrocycle, i.e. by changing the groups connecting two spirodiamides, by adjusting cavity size, or by adding bulkier alkyl X groups which provide high lipophilicity and much thicker ligand layer, greater Li+/Na+ selectivity can be obtained.

What is claimed is:

1. A compound of the formula

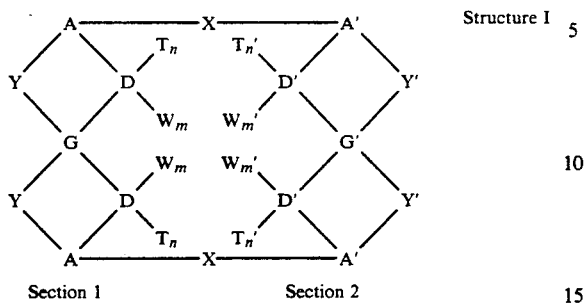

Structure I

Section 1          Section 2 wherein

A and A' independently represent carbon or nitrogen atoms;

D and D' independently represent carbon, nitrogen, oxygen, sulfur or phosphorus atoms;

G and G' independently represent carbon or silicon atoms;

T and T' independently represent an oxygen atom or a radical R;

W and W' independently represent an oxygen atom or a radical R;

R represents an alkyl or aryl group with from 1 to 12 carbon atoms, or OR' wherein O independently represents an oxygen atom and R' represents an alkyl or aryl group with from 1 to 12 carbon atoms;

m represents 0 or 1;

n represents 0 to 1;

Y and Y' independently represent a hydrocarbon or heterocarbon group having from 1 to 10 members, the members of Y and Y' selected from the group consisting of carbon, nitrogen, oxygen, sulfur and phosphorus; and X independently represents a hydrocarbon or heterocarbon group having from 3 to 10 members, the members of X selected from the group consisting of carbon, nitrogen, oxygen, sulfur and phosphorus; and A, A', D, D', $T_n$, $T'_n$, $W_m$ and $W'_m$ include sufficient bonds to adjacent atoms to lead to stable molecules.

2. The compound of claim 1 wherein Y and Y' are each represented by $(CH_2)_n$ with n=from 1 to 10.

3. The compound of claim 1 wherein Y and Y' include at least one fused hydrocarbon or fused heterocyclic ring.

4. The compound of claim 1 wherein X is selected from the group consisting of formulas a-p as follows:

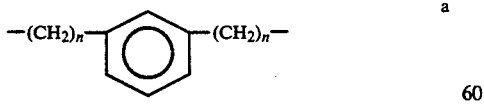

a

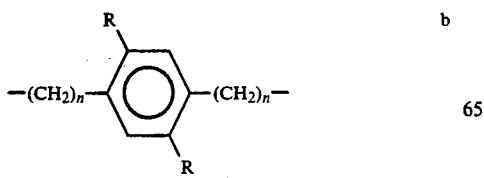

b

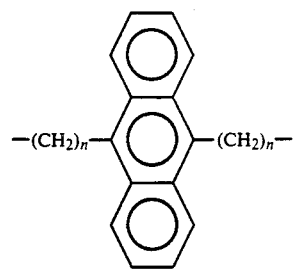

c

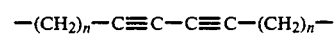

d

e

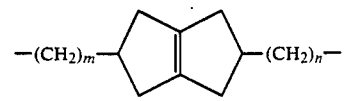

f

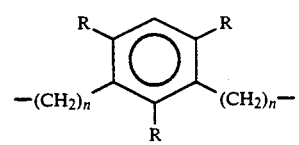

g

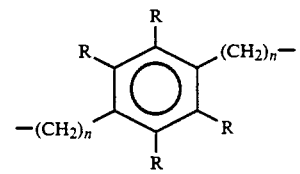

h

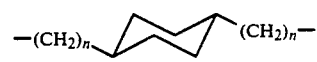

i

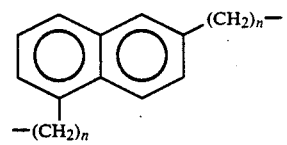

j

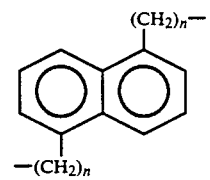

k

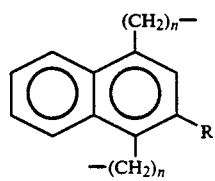

l

-continued

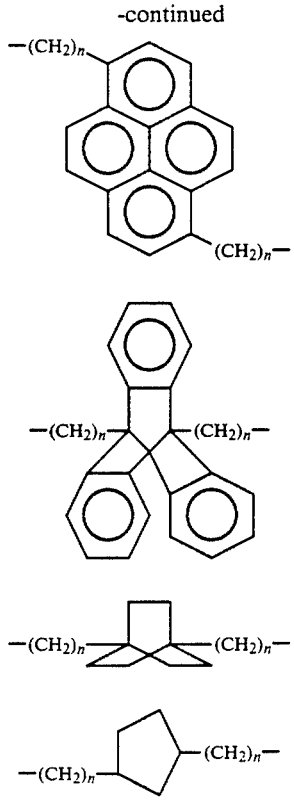

R = alkyl or aryl of $C_{1-12}$
n = 0-4.

5. The compound of claim 1 wherein X is selected from the group consisting of phenyl, dialkylphenyl, anthracenyl, acetylenic and diacetylenic groups.

6. The compound of claim 1 in which a binding portion of Structure I represented by

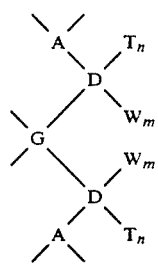

is selected from the group consisting of formulas i-xiii:

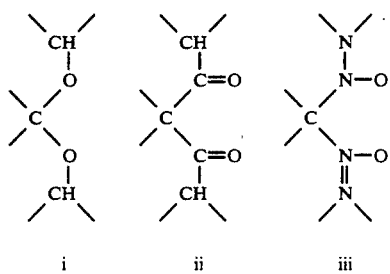

-continued

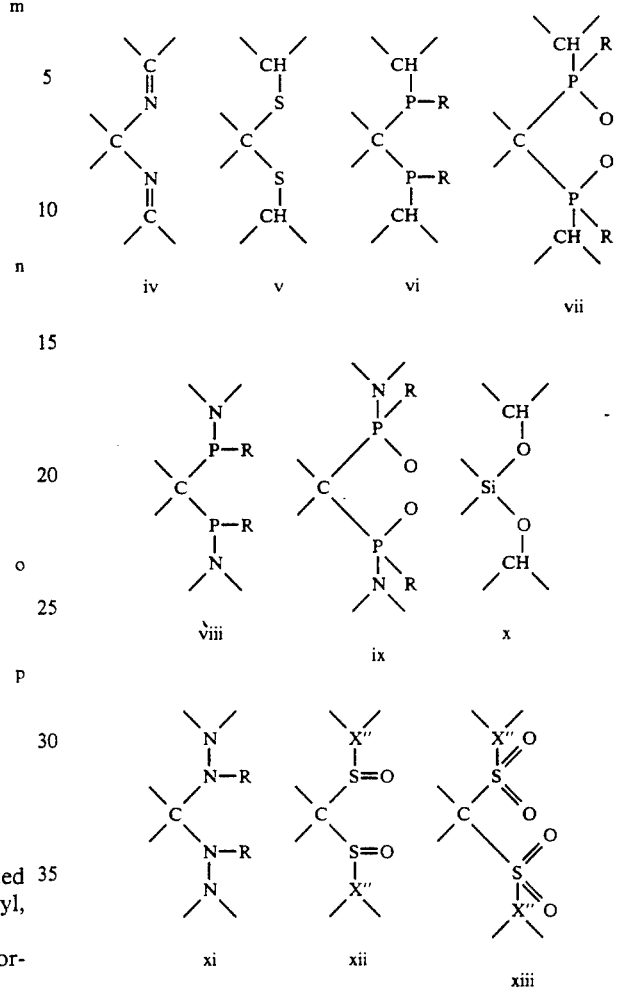

R = alkyl, aryl or OR' of $C_{1-12}$
X'' = CH or N.

7. The compound of claim 1 wherein Section 1 and Section 2 are independently selected from the group consisting of formulas xiv-xxiv:

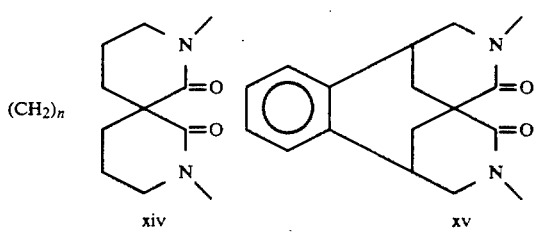

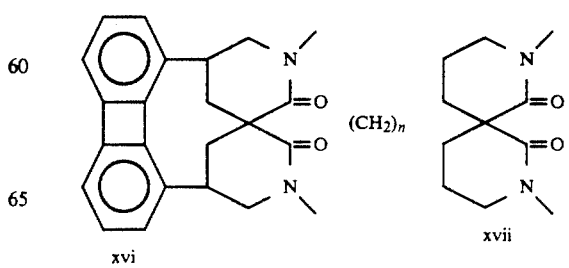

-continued

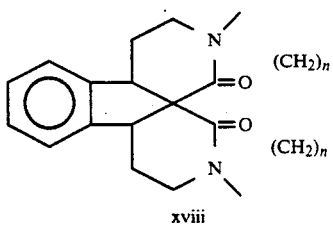 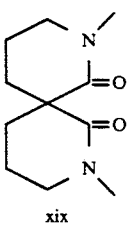

xviii     xix

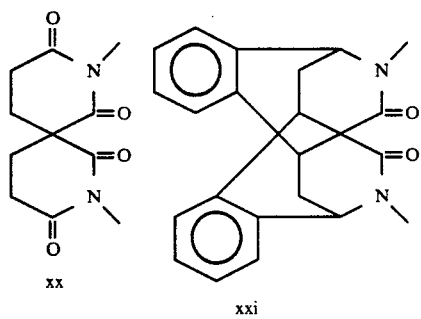

xx     xxi

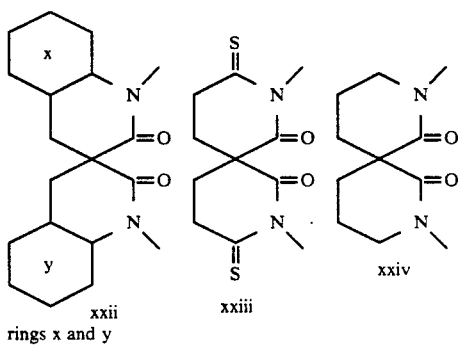

xxii    xxiii    xxiv rings x and y
are aromatic or saturated n = 1-10.

8. The compound of claim 1 having Structure A as follows:

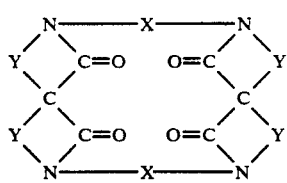  Structure A wherein:
C represents carbon atoms;
N represents nitrogen atoms;
O represents oxygen atoms;
Y is a hydrocarbon or heterocarbon radical having from 1 to 10 members selected from the group consisting of carbon, nitrogen, oxygen, sulfur and phosphorus;
X is a hydrocarbon or heterocarbon radical having from 3 to 10 members selected from the group consisting of carbon, nitrogen, oxygen, sulfur and phosphorus.

9. The compound of claim 1 wherein section 1 and section 2 represent formulas having the same atoms so that the molecule represented by structure I is symmetrical.

10. The compound of claim 1 wherein section 1 to section 2 represent formulas having different atoms so that the molecule represented by structure I is asymmetrical.

11. A complex having at least one Structure II and a cation complexed therewith, Structure II having the formula

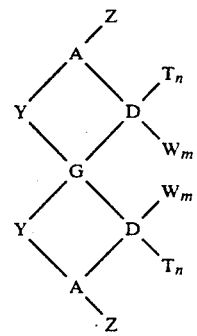

wherein:
A, D, G, T, W, R, m, n, and Y are defined as in claim 1 and Z independently represents a hydrocarbon or heterocarbon radical having at least two members.

12. The compound of claim 1 having the formula of compound 10:

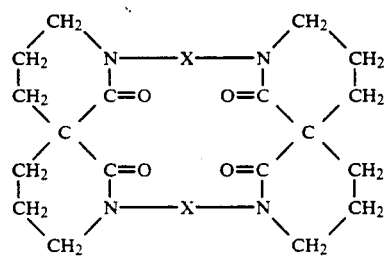

wherein:
X is a hydrocarbon or heterocarbon radical having from 3 to 10 members selected from the group consisting of carbon, nitrogen, oxygen, sulfur and phosphorous.

13. A complex comprising the compound of claim 1 and a cation complexed therewith.

14. The complex of claim 13 wherein the cation is a metal ion.

15. The complex of claim 14 wherein the metal ion is $Li^+$.

16. The complex of claim 1 having the formula

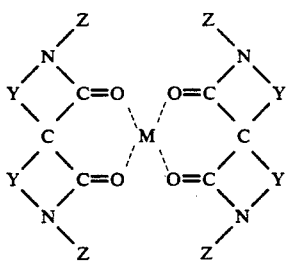  Structure C wherein:
C represents carbon atoms;
N represents nitrogen atoms;
O represents oxygen atoms:

M is a complexed cation,

Y is a hydrocarbon or heterocarbon radical having from 1 to 10 members, the members of Y selected from the group consisting of carbon, nitrogen, oxygen, sulfur and phosphorus; and Z is a hydrocarbon or heterocarbon radical having at least two members, the members of Z selected from the group consisting of carbon, nitrogen, oxygen, sulfur and phosphorus.

17. The complex of claim 16 wherein the cation is a metal ion.

18. The complex of claim 17 wherein the metal ion is $Li^+$.

19. The complex of claim 11 wherein Z is selected from the group consisting of —$CH_2Ph$, —$CHPh_2$, —$CPh_3$, -t-butyl, neopentyl, bicyclooct-1-yl, bicyclohept-1-yl and tryptycyl.

20. The complex of claim 13 having the formula

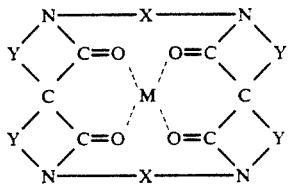

Structure B wherein:

C represents carbon atoms;

N represents nitrogen atoms;

O represents oxygen atoms;

Y is a hydrocarbon or heterocarbon radical having from 1 to 10 members, the members of Y selected from the group consisting of carbon, nitrogen, oxygen, sulfur and phosphorus;

X is a hydrocarbon or heterocarbon radical having from 3 to 10 members, the members of X selected from the group consisting of carbon, nitrogen, oxygen, sulfur and phosphorus; and M is a complexed cation.

* * * * *